US00PP11711P

United States Patent [19]

Bradford et al.

[11] Patent Number: Plant 11,711

[45] Date of Patent: Dec. 19, 2000

[54] NECTARINE TREE NAMED 'CRIMSON PEARL'

[76] Inventors: Lowell Glen Bradford, 12439 E. Savana Rd.; Norman G. Bradford, 11875 E. Savana Rd., both of Le Grand, Calif. 95333

[21] Appl. No.: 09/229,633

[22] Filed: Jan. 13, 1999

[51] Int. Cl.[7] ..... A01H 5/00

[52] U.S. Cl. ..... Plt./188

[58] Field of Search ..... Plt./188

[56] References Cited

U.S. PATENT DOCUMENTS

P.P. 9,359 11/1995 Bradford ..... Plt./188

OTHER PUBLICATIONS

Okie, W.R. Handbook of Peach and Nectarine Varieties, Springfield, VA pp. 375, 376, 646, 780, 787, May 1998.

*Primary Examiner*—Howard J. Locker
*Assistant Examiner*—Wendy A. Baker

[57] ABSTRACT

The present invention relates to a nectarine tree, *Prunus persica,* and more particularly to a new and distinct variety broadly characterized by a medium size, vigorous, self-fertile, productive and regular bearing tree. The fruit matures under the ecological conditions described approximately the first week in August, with first picking on Aug. 6, 1998. The fruit is uniformly large in size, subacidic and sweet in flavor, globose in shape, clingstone in type, very firm and crisp in texture, and mostly red in skin color. The variety was selected as an open pollinated seedling of an unnamed white flesh clingstone nectarine.

1 Drawing Sheet

BACKGROUND OF THE VARIETY

In a continuing effort to improve the quality of fresh market and shipping fruits, we, the inventors, typically hybridize a large number of nectarine and peach seedlings each year. We also grow a significant number of open pollinated seeds attempting to capture desired recessive traits. The present invention relates to a new and distinct variety of nectarine tree, which has been denominated varietally as 'Crimson Pearl'. The present variety was developed by us in 1992 in a cultivated area of our experimental orchard at Bradford Farms near Le Grand, Calif. in Merced County (San Joaquin Valley). It was selected as an open pollinated seedling grown from mixed seeds of unnamed white flesh clingstone nectarine seedlings from our breeding grounds. Subsequent to origination of the present variety of nectarine tree, we asexually reproduced it by budding and grafting on Nemaguard (unpatented) rootstock, in the experimental orchard described above, and such reproduction of plant and fruit characteristics were true to the original plant in all respects.

The fruit produced by the present variety is most similar to the 'Bright Pearl' (U.S. Plant Pat. No. 9,359) Nectarine by producing white flesh nectarines that are subacidic in flavor, clingstone in type, firm in texture, and almost full red in skin color, but is distinguished therefrom and an improvement thereon by producing fruit that ripens about two weeks later.

DRAWING

The accompanying photograph exhibits five whole fruits positioned to display the characteristics of the skin color and form, a sectioned fruit sliced transverse to the suture plane to reveal the flesh and stone, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), California, and was developed at the state of hard shipping ripe on Aug. 9, 1998. All major color code designations are by reference to the Inter-Society Color Council, National Bureau of Standards. Common color names are also used occasionally.

TREE

Size: Medium, reaching a height of 10' [3.05 meters] by the 6th year of growth, including typical dormant pruning.

Vigor: Vigorous, responding typically to irrigation and fertilization. The plant should be grown on a standard commercial rootstock for production purposes.

Growth: Upright and dense.

Form: Vase formed.

Hardiness: Hardy with respect to typical central California winters.

Production: Productive, thinning necessary.

Fertility: Self-fertile.

Bearing: Regular bearer, with no alternate bearing observed.

Trunk:

- *Size.*—Medium, reaching a maximum diameter of 4.5" [114 mm.] after 6 years of growth.
- *Texture.*—Medium to somewhat shaggy.
- *Bark color.*—Moderate brown [58. m.Br].
- *Lenticels.*—Numerous. Color: Brownish orange [54. brO]. Typical size: ⅛" to ⅜" [3.2–9.5 mm.].

Branches:

- *Size.*—Medium, typical of the species.
- *Texture.*—Smooth on 1st year wood, increasing roughness with age.
- *Color.*—1st Year Wood Topside: Light, purplish pink [249. l.pPk]. 1st Year Wood Underside: Light yellow green [119. l.YG]. Older Wood: Strong brown [55. s.Br].
- *Lenticels.*—Numerous, small. Color: Brownish orange [54. brO]. Average Size: 1/16" [1.6 mm.].

Leaves:

- *Size.*—Medium. Average Length: 5¼" [133.4 mm.]. Average Width: 1½" [38.1 mm.].
- *Thickness.*—Medium.
- *Form.*—Elliptical.
- *Apex.*—Acuminate.
- *Base.*—Acute.
- *Surface.*—Smooth.

*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: ½" [12.7 mm.]. Average Thickness: 1/16" [1.6 mm.]. Color: Light yellow green [119. l.YG].
*Stipules.*—2 per leaf bud, up to 6 at the growing tip. Average Length: ¼" [6.4 mm.].
*Glands.*—Numbers: 2 to 4 per leaf. Position: Some oppositely and some alternately positioned on petiole and base of blade. Size: Small. Form: Globose. Color: Light yellow green [119. l.YG].

Flower buds:
*Hardiness.*—Hardy with respect to central California winters.
*Diameter.*—Typically ⅜" [9.5 mm.] 1 week before bloom.
*Length.*—Typically ¾" [19.1 mm.] 1 week before bloom.
*Form.*—Free.
*Surface.*—Pubescent.

Flowers:
*Blooming period.*—Medium as compared to other varieties.
*Onset of bloom.*—One percent on Feb. 27, 1998.
*Duration of bloom.*—One to two weeks, dependent on ambient temperature.
*Type.*—Showy.
*Average diameter.*—1¾" [44.5 mm.].
*Color.*—Grayish purplish pink [253. gy.pPk].
*Fragrance.*—None to slight.

FRUIT

Maturity when described: Hard shipping ripe, Aug. 9, 1998.
Date of first picking: Aug. 6, 1998.
Date of last picking: Aug. 16, 1998.
Size: Uniform, large.
*Average diameter axially.*—2⅝" [66.7 mm.].
*Average transversely in suture plane.*—2⅝" [66.7 mm.].
*Typical weight.*—6.1 ounces [173 grams].
Form: Globose, slightly compressed laterally, mostly symmetrical with a few unsymmetrical.
*Longitudinal section form.*—Round.
*Transverse section through diameter.*—Round to elliptical.
Suture: An inconspicuous line toward the base becoming a deepening groove toward the apex, extending beyond the apex with a slight depression at the pistil point.
Ventral surface: Rounded, lipped toward the apex.
Lips: Most equal, but some unequal.
Cavity: Flaring, elongated in the suture plane, suture showing on one side, stem markings typical.
*Depth.*—½" [12.7 mm.].
*Breadth.*—¾" [19.1 mm.].
Base: Truncate.
Apex: Rounded.
*Pistil point: Very short, indented within the suture.*
Stem: Medium.
*Average length.*—⅜" [9.5 mm.].
*Average width.*—3/16" [4.8 mm.].
Skin:
*Thickness.*—Medium.
*Texture.*—Medium.
*Taste.*—Slightly astringent.
*Tenacity.*—Tenacious to flesh.
*Tendency to crack.*—None observed.
*Color.*—Very dark red [17. v.d.R] over a moderate red [15. m.R] background with pale yellow [89. p.Y] freckling more pronounced toward the apex.

Flesh:
*Color.*—Yellowish white [92. yWhite] with dark red [16. d.R] streaking toward the stone and some dark red [16. d.R] flecking scattered throughout.
*Surface of pit cavity.*—Dark red [16. d.R] fibers breaking when twisted away from the stone.
*Amygdalin.*—Wanting.
*Juice.*—Abundant, rich.
*Texture.*—Firm, crisp.
*Fibers.*—Abundant, fine.
*Ripens.*—Slightly earlier at the apex.
*Flavor.*—Subacid and very sweet, typically 17 to 21 brix.
*Aroma.*—Slight.
*Eating quality.*—Very good.

STONE

Type: Clingstone.
Form: Oval.
Base: Straight.
Apex: Acute.
Hilum: Narrow.
Sides: Slightly unequal.
Surface: Irregularly furrowed toward the apex, pitted from the center to the base.
Ridges: Jagged toward the base.
Color: Moderate brown [58. m.Br] when dry.
Pit wall: ¼" [6.4 mm.] thick.
Average width: Approximately 1".
Average length: Approximately 1¼".
Tendency to split: Slight in wet season.
Kernel:
*Form.*—Oval.
*Taste.*—Very bitter.
*Viable.*—Yes.
*Average width.*—½" [12.7 mm.].
*Average length.*—¾" [19.1 mm.].
*Skin color.*—Yellowish white [92. yWhite] with grayish brown [61. gy.Br] veins when first removed from stone.
*Pellicle color.*—Grayish brown [61. gy.Br].
*Amygdalin.*—Abundant.

USE

Market: Fresh and long distance shipping.
Keeping quality: Fruit quality observed to remain in good condition in excess of 17 days in cold room at 36° Fahrenheit [2° Celsius].
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to the Bright Pearl (U.S. Plant Pat. No. 9,359) Nectarine by producing white flesh nectarines that are subacidic in flavor, clingstone in type, firm in texture, and almost full red in skin color, but is distinguished therefrom and an improvement thereon by producing fruit that ripens about two weeks later.

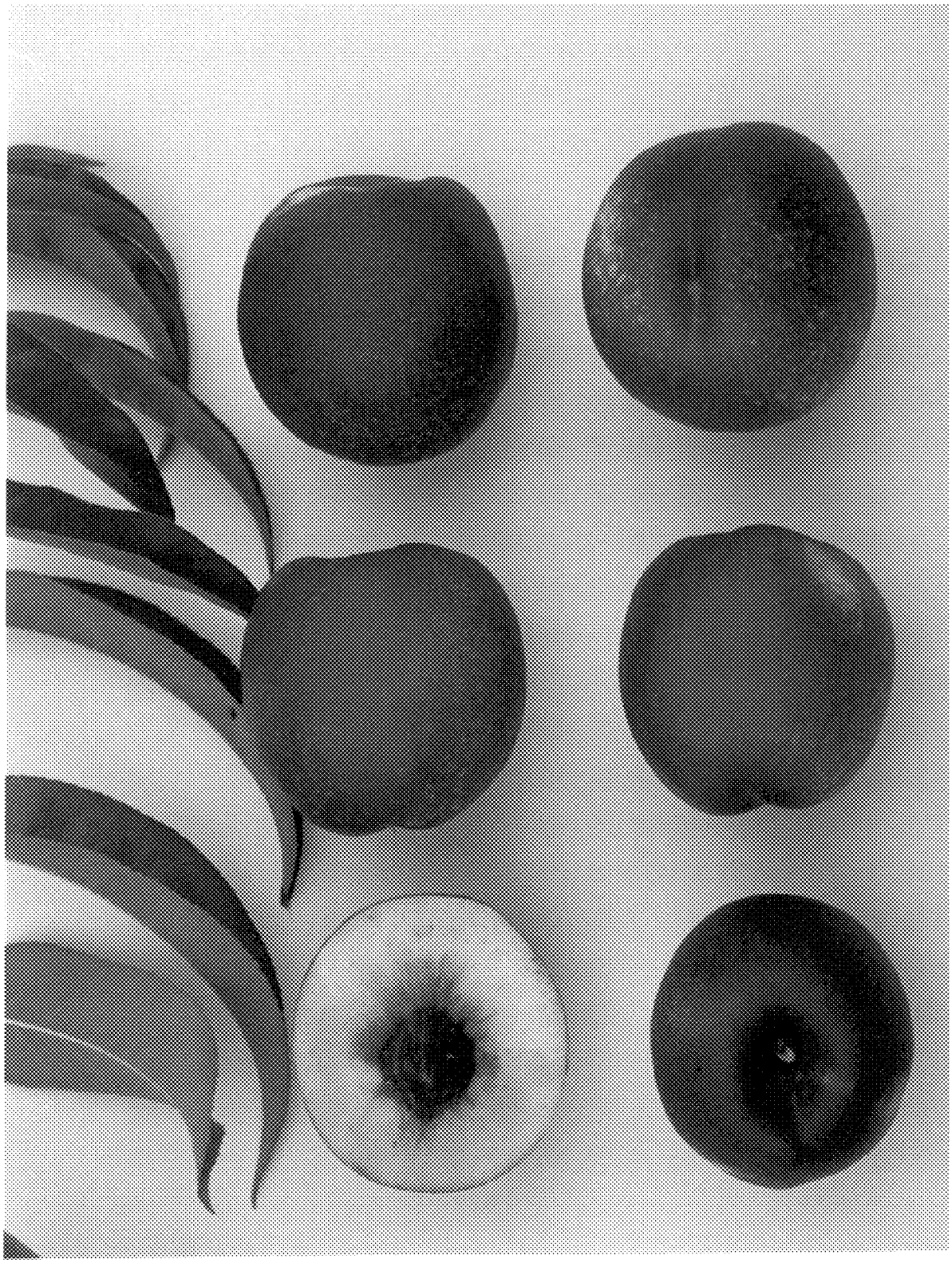

* * * * *